United States Patent [19]

Hlavka et al.

[11] Patent Number: 4,544,759

[45] Date of Patent: Oct. 1, 1985

[54] PLATINUM COMPLEXES OF ANTITUMOR AGENTS

[75] Inventors: Joseph J. Hlavka, Tuxedo; Panayota Bitha, Pomona; Yang-i Lin, Nanuet, all of N.Y.

[73] Assignee: American Cyanamid Company, Stamford, Conn.

[21] Appl. No.: 518,730

[22] Filed: Jul. 29, 1983

[51] Int. Cl.$^4$ ............... C07F 15/00; A01N 55/02; A61K 31/28

[52] U.S. Cl. .................. 556/36; 546/112; 548/109; 549/3; 549/206; 556/137; 556/32

[58] Field of Search ............. 260/429 R; 424/287

[56] References Cited

U.S. PATENT DOCUMENTS 3,892,790 7/1975 Tobe et al. ............ 260/429 R
3,904,663 9/1975 Tobe et al. ............ 260/429 R

OTHER PUBLICATIONS

Connors et al, Platinum Coordination Complexes in Cancer Chemotherapy, Springer Verlag, N.Y., pp. 34 & 35, (1974).
Chemical Abstracts 79, 26649z, (1973).
Chemical Abstracts 96, 134801c, (1982).
Chemical Abstracts 91, 116501z, (1979).
Chemical Abstracts 93, 230058z, (1980).

Primary Examiner—Helen M. S. Sneed
Attorney, Agent, or Firm—Edward A. Conroy, Jr.

[57] ABSTRACT

The compounds are the class of substituted hydrazine carboximidamides which are useful for inducing the regression and/or palliation of leukemia and related cancers in mammals when administered in amounts of from about one mg. to about 1.2 gm. per square meter of body surface area per day.

16 Claims, No Drawings

PLATINUM COMPLEXES OF ANTITUMOR AGENTS

SUMMARY OF THE INVENTION

This invention relates to platinum chelates of organic compounds which may be represented by the formula:

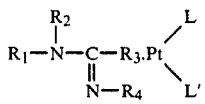

wherein $R_1$ is selected from the group consisting of amino, benzyl, cyano, $-CONH_2$, $-N=C(CH_3)_2$ and

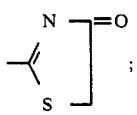

$R_2$ is selected from the group consisting of hydrogen and alkyl($C_1$–$C_3$); $R_3$ is selected from the group consisting of amino, hydrazino, dialkylamino($C_1$–$C_3$), nitroamino, alkyl($C_1$–$C_3$), phenyl, p-chlorophenyl, p-methoxyphenyl, phenylamino, benzylamino, alkylamino($C_1$–$C_3$), alkylthio($C_1$–$C_3$), diphenylamino, 2-thienylmethylamino, 2-furanylmethylamino, 2,3 and 4-pyridinylmethylamino and $-NH(CH_2)_nN(CH_3)_2$, where n is an integer 2–4; $R_4$ is selected from the group consisting of hydrogen and benzyl; and L and L' are the same or different and are selected from the group consisting of halide, nitrate, sulfate and a monobasic organic acid such as glucuronic acid, or L and L' taken together may be a dibasic organic acid such as malonic acid, oxalic acid, methyl malonic acid, succinic acid; 1,1-cyclobutane dicarboxylic acid or tartronic acid.

DETAILED DESCRIPTION OF THE INVENTION

The compounds of this invention may be prepared by treating the unchelated compounds with potassium tetrachloroplatinate in an aqueous medium for 12–48 hours.

The novel chelated compounds of the present invention possess the property of inhibiting the growth of transplanted mouse tumors as established by the following test.

Lymphocytic leukemia P388 test

The animals used were BDF/1 mice all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1,5 and 9, relative to tumor inoculation, at various doses. The animals were weighed and survivors recorded on a regular basis for 30 days. The median survival time and the ratio of survival time for treated (T)/control (C) animals were calculated. The positive control compound was either 1,4-dihydroxy-5,8-bis[[2-(2-hydroxyethylamino)ethyl]amino]anthraquinone dihydrochloride or Cisplatin.

The results of this test on representative compounds of this invention appear in Table I.

TABLE I

| Compound | Dose (mg/kg) | Median Survival (Days) | T/C × 100 (%) |
|---|---|---|---|
| hydrazinecarboximidamide, compound with platinum chloride (1:1) | 200 | 23 | 195 |
|  | 50 | 20.5 | 174 |
| Control | — | 11.8 | — |
| 1,4-dihydroxy-5,8-bis[[2-(2-hydroxyethylamino)ethyl]-amino]anthraquinone dihydrochloride | 1.6 | 25 | 212 |
|  | 0.4 | 18 | 153 |
|  | 0.1 | 16 | 136 |
|  | 0.025 | 13 | 110 |
| N—(2-pyridinylmethyl)hydrazinecarboximidamide, hydroiodide, compound with platinum chloride (1:1) | 200 | 14.5 | 119 |
|  | 50 | 15.5 | 127 |
|  | 12 | 15.5 | 127 |
|  | 3 | 15 | 123 |
| Control | — | 12.2 | — |
| Cisplatin | 1.5 | 22.5 | 184 |
|  | 0.8 | 26.5 | 217 |
| N—(phenylmethyl)hydrazinecarboximidamide, compound with platinum chloride (1:1) | 50 | 16 | 131 |
|  | 12 | 14.5 | 119 |
|  | 3 | 14 | 115 |
| Control | — | 12.2 | — |
| Cisplatin | 1.5 | 22.5 | 184 |
|  | 0.8 | 26.5 | 217 |
| carbonimidic dihydrazide compound with platinum chloride (1:1) | 200 | 81 | 168 |
|  | 50 | 15.5 | 145 |
|  | 12 | 12.5 | 117 |
|  | 3 | 13 | 121 |
| Control | — | 10.7 | — |
| Cisplatin | 2.5 | 16 | 150 |
|  | 1.2 | 22 | 206 |
|  | 0.6 | 21 | 196 |
| N—methylhydrazinecarboximidamide, compound with platinum chloride (1:1) | 200 | 16 | 150 |
|  | 50 | 14.5 | 136 |
|  | 12 | 13.5 | 126 |
|  | 3 | 12 | 112 |
| Control | — | 10.7 | — |
| Cisplatin | 2.5 | 16 | 150 |
|  | 1.2 | 22 | 206 |
|  | 0.6 | 21 | 196 |
| N,N—dimethylhydrazinedicarboximidamide, compound with platinum chloride (1:1) | 50 | 23.5 | 235 |
| Control | — | 10 | — |
| Cisplatin | 0.8 | 23.5 | 235 |
|  | 0.2 | 21 | 210 |
| N—[3-(dimethylamino)propyl]-hydrazinecarboximidamide, compound with platinum chloride (1:1) | 200 | 11.5 | 113 |
|  | 50 | 11 | 108 |
|  | 12 | 12 | 118 |
|  | 3 | 12 | 118 |
| Control | — | 10.2 | — |
| Cisplatin | 1.25 | 13.5 | 132 |
|  | 0.6 | 22.5 | 221 |
| N—(4-pyridinylmethyl)hydrazinecarboximidamide, compound with platinum chloride (1:1) | 200 | 12 | 118 |
|  | 50 | 12 | 118 |
|  | 12 | 11 | 108 |
| Control | — | 10.2 | — |
| Cisplatin | 1.25 | 13.5 | 132 |
|  | 0.6 | 22.5 | 221 |
| N—[2-(dimethylamino)ethyl]-hydrazinecarboximidamide, compound with platinum chloride (1:2) | 200 | 13 | 127 |
|  | 50 | 11.5 | 113 |
|  | 10 | 12 | 118 |
| Control | — | 10.2 | — |
| Cisplatin | 1.25 | 13.5 | 132 |
|  | 0.6 | 22.5 | 221 |
| N—(2-thienylmethyl)hydrazinecarboximidamide, compound with platinum chloride (1:1) | 200 | 15.5 | 152 |
|  | 50 | 15.5 | 152 |
|  | 12 | 12.5 | 123 |
| Control | — | 10.2 | — |
| Cisplatin | 1.25 | 13.5 | 132 |
|  | 0.6 | 22.5 | 221 |
| 1-methylhydrazinecarboximidamide, compound with platinum chloride (1:1) | 200 | 16.5 | 162 |
|  | 50 | 17 | 167 |
|  | 12 | 15.5 | 152 |
|  | 3 | 13 | 127 |
| Control | — | 10.2 | — |
| Cisplatin | 1.25 | 13.5 | 132 |
|  | 0.6 | 22.5 | 221 |

TABLE I-continued

| Compound | Dose (mg/kg) | Median Survival (Days) | T/C × 100 (%) |
|---|---|---|---|
| N—[(2-furanylmethyl)amino]-hydrazinecarboximidamide, compound with platinum chloride (1:1) | 200 | 11 | 108 |
| | 50 | 12 | 118 |
| Control | — | 10.2 | — |
| Cisplatin | 1.25 | 13.5 | 132 |
| | 0.6 | 22.5 | 221 |
| N—(3-pyridinylmethyl)hydrazinecarboximidamide, compound with platinum chloride (1:1) | 200 | 16.5 | 143 |
| | 50 | 13 | 113 |
| | 12 | 13.5 | 117 |
| | 3 | 13 | 113 |
| Control | — | 11.5 | — |
| Cisplatin | 1.25 | 25 | 217 |
| | 0.6 | 19 | 165 |
| N—phenylhydrazinecarboximidamide, compound with platinum chloride (1:1) | 50 | 14.5 | 126 |
| | 12 | 13.5 | 117 |
| | 3 | 13 | 113 |
| Control | — | 11.5 | — |
| Cisplatin | 1.25 | 25 | 217 |
| | 0.6 | 19 | 165 |
| | 3 | 13.5 | 117 |
| N,N—phenylhydrazinedicarboximidamide, compound with platinum chloride (1:1) | 200 | 13.5 | 117 |
| | 50 | 13 | 113 |
| | 12 | 13.5 | 117 |
| | 3 | 13.5 | 117 |
| Control | — | 11.5 | — |
| Cisplatin | 1.25 | 20 | 174 |
| | 0.6 | 25.5 | 222 |
| N,N'—bis(phenylmethyl)hydrazinecarboximidamide, compound with platinum chloride iodide (1:1) | 200 | 12.5 | 109 |
| | 12 | 12.5 | 109 |
| | 3 | 12 | 104 |
| Control | — | 11.5 | — |
| Cisplatin | 1.25 | 20 | 174 |
| | 0.6 | 25.5 | 222 |
| ethanimidic acid hydrazide, compound with platinum chloride (1:1) | 50 | 24.5 | 212 |
| | 12 | 23 | 200 |
| | 3 | 17.5 | 152 |
| Control | — | 11.5 | — |
| Cisplatin | 1.25 | 20 | 174 |
| | 0.6 | 25.5 | 222 |
| hydrazinecarboximidothioic acid methyl ester, compound with platinum chloride (1:1) | 200 | 13 | 113 |
| | 50 | 12.5 | 109 |
| | 3 | 12.5 | 109 |
| Control | — | 11.5 | — |
| Cisplatin | 1.25 | 20 | 174 |
| | 0.6 | 25.5 | 222 |
| (aminoiminomethyl)urea, compound with platinum chloride (1:1) | 200 | 21.5 | 201 |
| | 50 | 19.5 | 182 |
| | 12 | 17 | 159 |
| Control | — | 10.7 | — |
| Cisplatin | 3 | 16 | 150 |
| | 1.5 | 25.8 | 238 |
| | 0.8 | 18 | 168 |
| | 0.4 | 14.5 | 136 |
| cyanoguanidine, compound with platinum chloride (1:1) | 200 | 15.5 | 145 |
| | 50 | 13.5 | 126 |
| Control | — | 10.7 | — |
| Cisplatin | 3 | 16 | 150 |
| | 1.5 | 25.8 | 238 |
| | 0.8 | 18 | 168 |
| | 0.4 | 14.5 | 136 |
| benzenecarboximidic acid hydrazide compound with platinum chloride (1:1) | 50 | 15.5 | 152 |
| | 12 | 17 | 167 |
| | 3 | 14 | 137 |
| Control | — | 10.2 | — |
| Cisplatin | 2 | 27.5 | 270 |
| | 1 | 22 | 216 |
| | 0.5 | 20 | 191 |
| | 0.25 | 17 | 167 |
| 4-chlorobenzenecarboximidic acid hydrazide, compound with platinum chloride (1:1) | 50 | 17 | 167 |
| | 12 | 17 | 132 |
| | 3 | 13.5 | 132 |
| Control | — | 10.2 | — |
| Cisplatin | 2 | 27.5 | 270 |
| | 1 | 22 | 216 |
| | 0.5 | 20 | 196 |
| | 0.25 | 17 | 167 |
| 4-chlorobenzenecarboximidic acid, (1-methylethylidene)-hydrazide, compound with platinum chloride (1:1) | 200 | 14.5 | 142 |
| Control | — | 10.2 | — |
| Cisplatin | 2 | 27.5 | 270 |
| | 1 | 22 | 216 |
| | 0.5 | 20 | 196 |
| | 0.25 | 17 | 167 |
| 4-methoxy benzenecarboximidic acid, hydrazide, compound with platinum chloride (1:1) | 50 | 15.5 | 152 |
| | 12 | 17 | 167 |
| | 3 | 15.5 | 152 |
| Control | — | 10.2 | — |
| Cisplatin | 2 | 27.5 | 270 |
| | 1 | 22 | 216 |
| | 0.5 | 20 | 196 |
| | 0.25 | 17 | 167 |
| (4,5-dihydro-4-oxo-2-thiazolyl)guanidine, compound with platinum chloride (1:1) | 50 | 20 | 196 |
| | 12 | 16.5 | 162 |
| | 3 | 13 | 127 |
| Control | — | 10.2 | — |
| Cisplatin | 2 | 21 | 206 |
| | 0.5 | 17 | 167 |
| | 0.125 | 13.5 | 132 |
| N—nitrohydrazinecarboximidamide, compound with platinum chloride (1:1) | 50 | 22 | 206 |
| | 12 | 18.5 | 173 |
| | 3 | 16 | 150 |
| Control | — | 10.7 | — |
| Cisplatin | 3 | 16 | 150 |
| | 1.5 | 25.8 | 238 |
| | 0.8 | 18 | 168 |
| | 0.4 | 14.5 | 136 |

This aspect of the invention includes the novel compositions of matter and the method of inducing the regression and/or palliation of leukemia and related cancers in mammals when administered in amounts ranging from about one mg to about 1.2 gm per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219-244, May 1966. A preferred dosage regimen for optimum results would be from about 3 mg/m²/day to about 200 mg/m²/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daly dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

N-[3-(dimethylamino)propyl]hydrazinecarboximidamide, compound with platinum chloride (1:1)

A 953 mg portion of 1-amino-3-(dimethylaminopropyl)guanidine, dihydrobromide was dissolved in 20 ml of water and 324 mg of sodium methoxide was added, followed by 1.245 g of potassium tetrachloroplatinate. The resulting solution was stirred overnight and the solid recovered by filtration, giving 730 mg of the desired product.

Following the procedure of Example 1 and using the indicated precursors which are commercially available or literature compounds, and in some instances dimethylformamide as a cosolvent the products of Examples 2-14, found in Table II were prepared.

TABLE II

| Example | Precursor | Product | MP °C. |
|---|---|---|---|
| 2 | 1-amino-3-(4-pyridinyl-methyl)quanidine, dihydrochloride | N—(4-pyridinylmethyl)hydrazinecarboximidamide, compound with platinum chloride (1:1) | |
| 3 | 3-amino-1,1-diphenyl-guanidine, hydroiodide | N,N—phenylhydrazinecarboximidamide, compound with platinum chloride (1:1) | 198-202 |
| 4 | 1-amino-2,3-dibenzyl-guanidine, hydroiodide | N,N'—bis(phenylmethyl)hydrazinecarboximidamide, compound with platinum chloride iodide (1:1) | 248-255 |

TABLE II-continued

| Example | Precursor | Product | MP °C. |
|---|---|---|---|
| 5 | S—methylthiosemicarbazide, dihydrochloride | hydrazinecarboximidothioic acid, methyl ester, compound with platinum chloride (1:1) | |
| 6 | carbonimidic dihydrazide | carbonimidic dihydrazide, compound with platinum chloride (1:1) | |
| 7 | N,N—dimethylhydrazinecarboximidamide | N,N—dimethylhydrazinecarboximidamide, compound with platinum chloride (1:1) | |
| 8 | 1-amino-3-(2-dimethylaminoethyl)guanidine, trihydrochloride | N—[2-(dimethylamino)ethyl]-hydrazinecarboximidamide, compound with platinum chloride (1:2) | 223–240 |
| 9 | 1-amino-1-methylquanidine, hydrobromide | 1-methylhydrazinecarboximidamide, compound with platinum chloride (1:1) | >200 |
| 10 | 1-amino-3-furfurylguanidine, dihydrochloride | N—[(2-furanylmethyl)amino]-hydrazinecarboximidamide, compound with platinum chloride (1:1) | >300 |
| 11 | 1-amino-3-(2-thienylguanindine, dihydrochloride | N—(2-thienylmethyl)hydrazinecarboximidamide, compound with platinum chloride (1:1) | >200 |
| 12 | 1-amino-3-(3-pyridinyl-methyl)guaninidine, dihydrobromide | N—(3-pyridinylmethyl)hydrazinecarboximidamide, compound with platinum chloride (1:1) | |
| 13 | 1-amino-3-phenylguanidine, dihydrochloride | N—phenylhydrazinecarboximidamide, compound with platinum chloride (1:1) | >200 |
| 14 | ethanimidic acid hydrazide, hydrochloride | ethanimidic acid hydrazide, compound with platinum chloride (1:1) | >220 |

EXAMPLE 15

(Aminoiminomethyl)urea, compound with platinum chloride (1:1)

A solution of 306 mg of quanyl urea and 1.245 g of potassium tetrachloroplatinate in 15 ml of water was stirred overnight. The solid was collected, washed with water and dried, giving 400 mg of the desired product.

Following the procedure of Example 15, the products of Examples 16–22 found in Table III were prepared, in some instances using N,N-dimethylformamide to solubilize the starting material and using the indicated precursors which are commercially available or literature compounds.

EXAMPLE 23

N-Methylhydrazinecarboximidamide, compound with platinum chloride (1:1)

A 374 mg portion of N-amino-N'-methylguanidine hydrochloride was dissolved in 30 ml of 0.1N sodium hydroxide. To this solution was added 1.245 g of potassium tetrachloroplatinate. This suspension was stirred at room temperature overnight and then the solid was collected, washed with water and dried giving 710 mg of the desired product, mp 215° C. (dec.).

TABLE II

| Example | Precursor | Product | MP °C. |
|---|---|---|---|
| 16 | 1-amino-3-nitroguanidine | N—nitrohydrazinecarboximidamide, compound with platinum chloride (1:1) | |
| 17 | cyanoguanidine | cyanoguanidine, compound with platinum chloride (1:1) | |
| 18 | benzenecarboximidic acid hydrazide, monohydroiodide | benzenecarboximidic acid hydrazide, compound with platinum chloride (1:1) | |
| 19 | aminoguanidine, hydrochloride | hydrazinecarboximidamide, compound with platinum chloride (1:1) | 302 (dec.) |
| 20 | 1-amino-3-(2-pyridinyl-methyl)guanidine, dihydrochloride | N—(2-pyridinylmethyl)hydrazinecarboximidamide, compound with platinum chloride (1:1) | >250 |
| 21 | benzylaminoguanidine, dihydrochloride | N—(phenylmethyl)hydrazinecarboximidamide, compound with platinum chloride (1:1) | >250 |
| 22 | 1-(4-oxo-2-thiazolin-2-yl)-guanidine | (4,5-dihydro-4-oxo-2-thiazolyl)-guanidine, compound with platinum chloride (1:1) | |

EXAMPLE 24

4-Chlorobenzenecarboximidic acid hydrazide, compound with platinum chloride (1:1)

A mixture of 55.03 g of 4-chlorobenzonitrile, 75.13 g of thioacetamide and 600 ml of dimethylformamide was saturated with dry hydrogen chloride gas while being chilled in an ice bath. The mixture was then distilled slowly on an oil bath at 100° C. When the liquid had been removed, aqueous sodium bicarbonate was added. The solid was collected and recrystallized from toluene, giving 48.35 g of 4-chlorothiobenzamide as yellow crystals.

A 17.16 g portion of 4-chlorothiobenzamide was dissolved in 80 ml of acetone and 15.14 g of methyl iodide was added. The mixture was stirred for 2 hours and then the solid was collected, washed with acetone and dried, giving 21.3 g of 4-chlorobenzenecarboximidothioic acid, methyl ester, hydroiodide.

To a cold solution of 2.5 ml of hydrazine hydrate in 25 ml of ethanol was added 15.68 g of the above methyl ester. This mixture was stirred in an ice bath for 1.5 hours, then at room temperature for 2.5 hours and then filtered. The filtrate was added to 500 ml of anhydrous ether and refrigerated overnight. The solid was collected, washed with ether and dried, giving 13.3 g of 4-chlorobenzenecarboximidic acid hydrazide, monohydroiodide.

An 800 mg portion of the above hydrazide, together with 456.8 mg of silver nitrate was reacted as described in Example 15, giving 944 mg of the desired product.

EXAMPLE 25

4-Chlorobenzenecarboximidic acid (1-methylethylidene)hydrazide, compound with platinum chloride (1:1)

To a suspension of 5.95 g of 4-chlorobenzene carboximidic acid hydrazide, monohydroiodide in 30 ml of water and 10 ml of ethanol was added a solution of 3.39 g of silver nitrate in 10 ml of water. The mixture was stirred and then filtered. The pH of the filtrate was adjusted to 6.0 with sodium hydroxide and then to 2.0 with hydrochloric acid, then filtered and evaporated to dryness. The residue was dissolved in 20 ml of water and refrigerated overnight. The solid was recrystallized from ethanol, then acetone and dried, giving 3.04 g of the corresponding monohydrochloride derivative. This compound was reacted as described in Example 15 with the addition of 5 ml of ethanol, giving 317 mg of the desired product.

EXAMPLE 26

4-Methoxybenzenecarboximidic acid hydrazide, compound with platinum chloride (1:1)

A mixture of 53.26 g of anisonitrile and 60.10 g of thioacetamide in 600 ml of dimethylformamide was saturated with dry hydrogen chloride gas while being cooled in an ice bath. The mixture was then distilled on an oil bath at 100° C. After the liquid had been removed, aqueous sodium bicarbonate was added and the solid was collected and recrystallized from toluene, giving 50.47 g of 4-methoxythiobenzamide as a yellow solid.

A 16.7 g portion of 4-methoxythiobenzamide was converted to 4-methoxybenzenecarboximidothioic acid, methyl ester, monohydroiodide and futher converted to 4-methoxybenzenecarboximidic acid hydrazide monohydroiodide, by the procedure of Example 24. This hydrazide was then converted to the final product by the procedure of Example 25, giving 1.26 g.

EXAMPLE 27

N-[3-(Dimethylamino)propyl]hydrazinecarboximidamide, compound with potassium nitrate (1:1)

To a suspension of 1 m mole of the platinum chelate (Example 1) in 50 ml of water is added 2 m moles of silver nitrate. The mixture is stirred for 3 hours and then filtered. The filtrate is evaporated to dryness giving the desired product.

To obtain the organic acid derivative the nitro derivative is stirred with one molar equivalent of the potassium salt of a dibasic acid or two molar equivalents of the potassium salt of a monobasic acid in an aqueous medium.

We claim:

1. A compound of the formula:

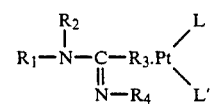

wherein $R_1$ is amino, benzyl, cyano, $-CONH_2$ or $-N=C(CH_3)_2$; $R_2$ is hydrogen or alkyl($C_1$-$C_3$); $R_3$ is amino, hydrazino, dialkylamino($C_1$-$C_3$), nitroamino, alkyl($C_1$-$C_3$), phenyl, p-chlorophenyl, p-methoxyphenyl, phenylamino, benzylamino, alkylamino($C_1$-$C_3$), alkylthio($C_1$-$C_3$), diphenylamino or $-NH(CH_2)_nN(CH_3)_2$ where n is an integer 2–4; $R_4$ is hydrogen or benzyl; and L and L' are the same and are anions selected from the group consisting of halide, nitrate, sulfate and ($C_2$-$C_6$)alkanoate or L and L' taken together is a dibasic anion selected from the group consisting of oxalate, malonate, methylamalonate, ethylmalonate, succinate, tartronate, 1,1-cyclopropane dicarboxylate and 1,1-cyclobutane dicarboxylate.

2. The compound according to claim 1; hydrazinecarboximidamide, compound with platinum chloride (1:1).

3. The compound according to claim 1; carbonimidic dihydrazide, compound with platinum chloride (1:1).

4. The comound according to claim 1; N-methylhydrazinecarboximidamide, compound with platinum chloride (1:1).

5. The compound according to claim 1; N,N-dimethylhydrazinedicarboximidamide, compound with platinum chloride (1:1).

6. The compound according to claim 1; 1-methylhydrazinecarboximidamide, compound with platinum chloride (1:1).

7. The compound according to claim 1; ethanimidic acid hydrazide, compound with platinum chloride (1:1).

8. The compound according to claim 1; (aminoiminomethyl)urea, compound with platinum chloride (1:1).

9. The compound according to claim 1; cyanoguanidine, compound with platinum chloride (1:1).

10. The compound according to claim 1; benzenecarboximidic acid hydrazide, compound with platinum chloride (1:1).

11. The compound according to claim 1; 4-chlorobenzenecarboximidic acid, compound with platinum chloride (1:1).

12. The compound according to claim 1; 4-chlorobenzenecarboximidic acid, (1-methylethylidine)-hydrazide, compound with platinum chloride (1:1).

13. The compound according to claim 1; 4-methoxybenzenecarboximidic acid, hydrazide, compound with platinum chloride (1:1).

14. The compound according to claim 1; N-nitrohydrazinecarboximidamide, compound with platinum chloride (1:1).

15. A method of inducing regression of leukemia cell growth or inhibiting growth of solid tumors in a mammal which comprises administering to said mammal an effective amount of a compound according to claim 1.

16. A pharmaceutical composition in dosage unit form useful for inducing regression of leukemia cell growth or inhibiting growth of solid tumors in a mammal which comprises from about 3 mg/m$^2$ per day to about 200 mg/m$^2$ per day of a compound according to claim 1 in combination with a pharmacologically acceptable carrier.

* * * * *